United States Patent [19]

Wagner et al.

[11] 4,366,703

[45] Jan. 4, 1983

[54] METHOD AND APPARATUS FOR DETERMINING PERMEABILITY AND THICKNESS OF REFRACTORY COATINGS ON FOUNDRY MOLDS AND CORES

[75] Inventors: Clifford G. Wagner, Clifton Park; Dallas E. Cain, Scotia, both of N.Y.

[73] Assignee: General Electric Company, Schenectady, N.Y.

[21] Appl. No.: 225,984

[22] Filed: Jan. 19, 1981

[51] Int. Cl.³ .............................................. G01N 15/08
[52] U.S. Cl. .......................................................... 73/38
[58] Field of Search ..................................... 73/38, 37.5

[56] References Cited

U.S. PATENT DOCUMENTS

| | | | |
|---|---|---|---|
| 2,659,433 | 11/1953 | Brown | 73/38 X |
| 3,056,281 | 10/1962 | Smyth | 73/38 |
| 3,808,876 | 5/1974 | Kershaw | 73/38 |
| 3,889,521 | 6/1975 | Jakimowicz | 73/38 |

*Primary Examiner*—Edward R. Kazenske
*Assistant Examiner*—Joseph W. Roskos
*Attorney, Agent, or Firm*—John F. Ahern

[57] ABSTRACT

A simple, easily operated method and apparatus for determining the thickness and gas permeability of refractory coatings as such coatings are in place on foundry molds and cores. The apparatus is entirely portable, requires no connections to utility supplies such as electricity, air sources and so forth, and is hand-held during operation. The apparatus comprises a hand-held probe having an outlet orifice of known, predetermined size for making contact with the mold and a hand-held measuring unit which includes a cylinder having a gravity-actuated piston, a gas flow rate meter, and a gravity-actuated check valve. The two separate hand-held units are interconnected by flexible conduit. The cylinder and piston combination cause a flow of air at controlled pressure through the mold at the probe contact surface. In operation, the piston is actuated by inverting the hand held measuring unit and then reinverting to its normal position. To estimate refractory coating thickness, known relationships between permeability and thickness are utilized following their establishment by independent methods of measuring coating thickness.

8 Claims, 2 Drawing Figures

METHOD AND APPARATUS FOR DETERMINING PERMEABILITY AND THICKNESS OF REFRACTORY COATINGS ON FOUNDRY MOLDS AND CORES

BACKGROUND OF THE INVENTION

This invention relates to a method and apparatus for measuring the permeability and for estimating the thickness of refractory coatings which have been applied to a porous substrate such as a foundry sand mold or core.

In preparing a foundry mold or core to produce a cast metal part, refractory coatings may be applied to the surface of the mold or core so that the molten metal is presented with a high quality contact surface. A properly applied coating of the correct thickness and permeability prevents defects such as penetration of the molten metal into the mold, spalling of the mold into the metal, and the passage of gas in either direction. The result is a greater yield of castings free of defects such as non-metallic inclusions, pinholes, pocks and so forth.

These refractory coatings consist essentially of a suspension of finely divided materials such as silica or zircon in water or isopropyl alcohol (or other suitable carriers), but may also contain certain well-known additives to improve rheological properties and shelf life. The coating is applied to the mold or core by painting, spraying, dipping, or by any number of available methods. Once in place, the coating is dried by the application or generation of heat or by simply allowing the liquid portion to evaporate at room temperature. The application and drying procedure is repeated as many times as necessary to build up the desired thickness of refractory coating.

The ability of the refractory coating to improve casting quality has been found to depend on many factors; chief among these are the thickness of the coating and its permeability. If the refractory coating is too thin, there is the possibility of metal penetration; if the coating is too thick, there may be "wash crazing" and spalling. On the other hand, permeability of the coating layer exerts direct control on the movement of gas at the mold-metal interface and, therefore, on certain gas related defects such as blows and pocks. For example, when permeability is too low, gas can become trapped in a sector of the mold causing incomplete fill defects.

Heretofore, instruments and devices known to measure these two characteristics of the coating layer on a foundry mold or core have been deficient in some significant respect. For example, instruments easily movable to make measurements from place to place on a large mold or core have not been available. Portability is of particular importance in certain foundry operations in which very large castings are made. For example, it is not uncommon in producing parts for a large steam turbine for foundry personnel to actually move from place to place inside a large mold in an attempt to gather permeability and refractory coating thickness data. Still further, in obtaining mold or core permeability data with many of the prior art devices the mold or core may be rendered useless (but damaged in any case) after testing since the mold or core of interest must be damaged or destroyed to accommodate the test apparatus. In this regard, see U.S. Pat. Nos. 2,659,433; 3,172,258; 3,181,346 which are of potential interest for permeability testing but which require destructive sampling of the mold or core. It is clear, too, that the apparatus of these patents, as well as that of U.S. Pat. No. 3,335,787, (which is a complicated automatic compactor-tester) have no potential use for measuring the permeability of a refractory coating in place on a mold or core.

In other fields, not directly related to foundry processes, devices have been devised for testing the gas permeability of such materials as paper and fabric. For instance, in U.S. Pat. No. 3,808,876 a permeability tester is disclosed for testing the permeability of a surface material such as paper or cloth. While seemingly portable, the permeability tester of U.S. Pat. No. 3,808,876 requires a source of compressed air (not shown in the patent specification) which limits its portability. Further, use of such a device is not as straightforward as would be desired for foundry use since there is a necessity for finely adjusting a vacuum-box or needle-valve to achieve essentially uniform measuring pressure as determined by a vacuum or pressure gage. Furthermore, the required use of precision fitted parts, such as the needle-valve, contribute to long-term unreliability when operating in the inherently dirty, dusty environment of a foundry.

In U.S. Pat. No. 4,191,046 there is disclosed a permeability tester directed principally to permeability measurements on cigarette papers. In this device, the paper under test is mounted in a paper clamping head and air pressure is adjusted to a standard test pressure while the air flow rate is noted. Thus, many of the drawbacks of the above-noted patent U.S. Pat. No. 3,808,876 are present in this latter disclosed paper testing apparatus.

It is, therefore, among the objects of the present invention to provide a simple, easily operated method and apparatus for determining the thickness and gas permeability of refractory coatings as such coatings are in place on foundry molds and cores. Still further, it is an object of the invention to provide apparatus for carrying out such determinations which is entirely portable, requires no connections to utility supplies such as electricity, air sources and so on, and which is hand-held during operation. still further objects of the invention will become apparent from the ensuing description.

As sometimes used herein, the generic term "mold" will be intended to encompass both mold and cores—the latter being recognized as that part of a mold which forms the interior of a hollow casting.

SUMMARY OF THE INVENTION

These and other objects are attained by providing a hand-held probe having an outlet orifice of known, predetermined size for making contact with the mold at the location at which permeability and coating thickness are to be determined. The probe is connected by flexible conduit to a hand-held unit which includes a cylinder having a gravity-actuated piston, a gas flow-rate meter, and a gravity-actuated check valve. The cylinder and piston combination supplies air to force a flow stream at controlled pressure through the mold at the probe contact surface. The flow-meter, series connected between the cylinder and probe, contains a scale calibrated in terms of air flow rate or permeability.

In operation, the hand held unit (including the cylinder, piston, check valve, and flow meter) is first inverted to position the piston at one end of the cylinder and to open the check valve to allow air to enter the cylinder on the underside of the piston. With the hand held unit returned to a non-inverted or upright position, the piston begins to fall under the influence of gravity, generating substantially constant air pressure and forcing air through the mold as it is contacted by the probe. To estimate coating thickness, known relationships between permeability (obtained from the flowmeter) and thickness are utilized. Such relationships are pre-established by independent methods of measuring coating thickness.

BRIEF DESCRIPTION OF THE DRAWINGS

While the specification concludes with claims particularly pointing out and distinctly claiming the subject matter regarded as the invention, the invention will be better understood from the following description taken in connection with the accompanying drawings in which:

DETAILED DESCRIPTION OF THE INVENTION

Figure 1:
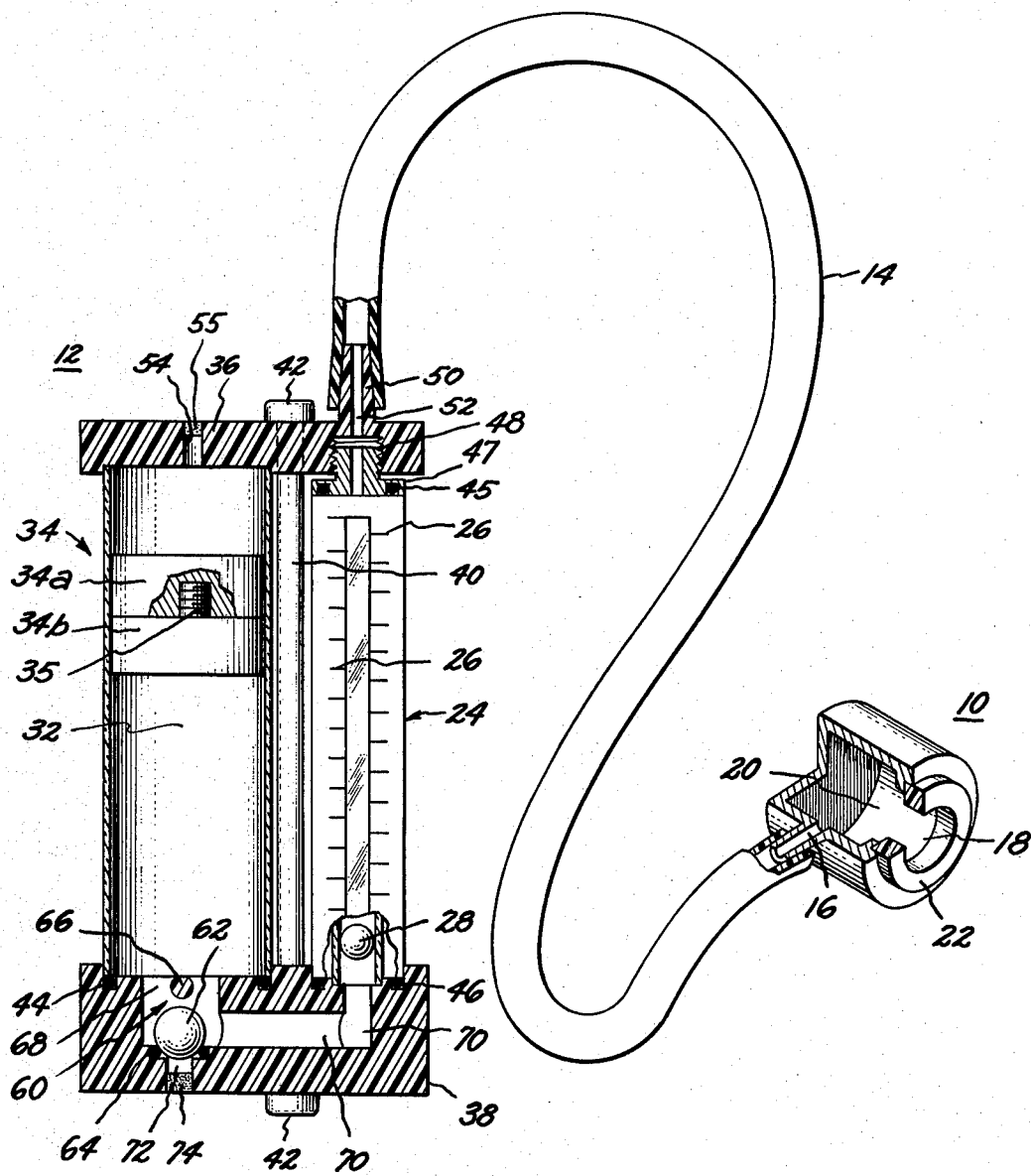
FIG. 1 illustrates, partially in cross-section and partially in cut-away, apparatus according to the present invention.

A preferred embodiment of the invention, as illustrated in FIG. 1, is generally divided into a hand-held probe 10 for making contact with the mold or core under examination and a hand-held measuring unit 12 which is operable to perform the measuring function. The two hand-held portions 10 and 12 are interconnected by fairly stiff-walled but flexible conduit 14. For example, conduit 14 may be rubber or plastic tubing. The hand-held probe 10 includes a side mounted inlet connection 16 for attaching one end of the flexible conduit 14 and an outlet orifice 18 of preselected area for contacting the mold or core under test (not specifically illustrated). The probe 10 is generally of cylindrical shape and is substantially hollow to define a passageway 20 fluidly interconnecting the inlet 16 and the outlet orifice 18. A resilient sealing ring 22 is concentrically affixed around the outlet orifice 18 to provide a sealed contact between the probe 10 and the mold or core. The sealing ring 22 resiliently conforms to small irregularities in the surface at the contact area as the ring 22 is lightly compressed under pressure from the operator's hand. The inside diameter of sealing ring 22 defines the surface area whose permeability is being determined.

The hand-held measuring unit 12 includes a variable area type flowmeter 24 which has a measuring scale 26 imprinted or otherwise marked thereon and a ball flow indicator 28 whose displacement upward in the flowmeter 24 is indicative of the rate of fluid flow therein. As will be more fully discussed herein below, measuring scale 26 is calibrated in terms of air permeability. Also included as part of hand-held measuring unit 12, is cylinder 32 fitted with an internal, free-floating piston 34. The piston 34 is close fitted within the cylinder 32 to prevent fluid flow between the walls of cylinder 32 and the perimeter of piston 34. However, piston 34 is free to slide from end to end in the cylinder 32 under the force of its own weight. Piston 34 is divided into first and second portions 34a and 34b, respectively, which are held together by threaded stud 35. First portion 34a is therefore separable from second portion 34b and may be replaced with other, identically constructed pieces, but of different density, to alter the weight of piston 34.

Preferably, cylinder 32 is of a transparent material so that the position of piston 34 can be observed at all times.

Cylinder 32 and flowmeter 24 are fitted at their ends with a top end piece 36 and a bottom end piece 38 which are held together with an interconnecting rod 40 having, for example, retainer nuts 42 at each end. Resilient sealing gaskets 44, 45, and 46 are provided, respectively, at the bottom end of cylinder 32, and at the top and bottom ends of flowmeter 24. These gaskets 44, 45, and 46 are lightly compressed by tightening units 42 on rod 40 and thereby preventing air leakage. To permit quick removal of flowmeter 24, ring 47, having mating threads 48 with top end-piece 36, is provided. Ring 47 is screwed further into end-piece 36 to perovide clearance for removal and replacement of flowmeter 24. Upon replacement, ring 47 is retracted from end-piece 36 to compress gasket 45, providing sealing and retention of the flowmeter 24. Top end piece 36 has an outlet fitting 50 including an internal passageway 52 which puts flowmeter 24 in fluid communication with the flexible conduit 14.

Piston 34 is freely slidable between a first end at the top of cylinder 32 and a second end at the bottom of cylinder 32. The first, or top end of cylinder 32 is open to the atmosphere by virtue or orifice 54 which passes through top end piece 36. A small packing of filter material 55 prevents dirt and other contaminants from entering cylinder 32. Located at the second, or bottom end of cylinder 32 and within the bottom end piece 38 is a gravity operated check valve 60. Check valve 60 includes ball 62; valve seal ring 64 which is of a resilient material forming a seal with ball 62 whenever the ball 62 is in the rest position illustrated; and ball stop pin 66 which retains ball 62 within check valve cavity 68 irrespective of the position of the hand-held unit 12. Cavity 68 is fluidly connected to the second end of cylinder 32 and, by passageway 70, is fluidly connected to the entrance end of flowmeter 24. An air inlet orifice 72 is provided in bottom end piece 38 and fluidly connects check valve cacity 68 with the atmosphere through a filter medium 74 whenever ball 62 is removed from seat ring 64. Ball stop pin 66 is removable (for example, by threading into end piece 38) for assembly of the check valve 60.

In operation, the outlet orifice end of probe 10 is placed on the area of the mold or core whose permeability is to be measured and is held in place with one hand. The hand-held measuring unit 12, easily manipulated by the other hand, is turned upside down causing piston 34 to move to the first end of the cylinder 32 and the ball check valve 60 to open (ball 60 comes off of seat-ring 64) allowing outside air to enter the second end of cylinder 32 through filter 74, orifice 72, and cavity 68. After the piston 34 has come to rest against the first end of cylinder 32, and while holding the probe 10 firmly against the area to be tested, the hand-held unit 20 is turned back over to its normal vertical position. This causes the check valve 60 to close (ball 62 is returned to rest upon seat ring 64) and the air in cylinder 32 is driven at substantially constant pressure through passageway 70, flowmeter 24, conduit 14, and finally from probe 10 through the area of core or mold under test. As the air passes through flowmeter 24, ball 28 is forced to rise an amount proportional to the rate of air flow, indicative thereby of the permeability of the test piece to air.

The range of permeability values that can be measured is determined by the range of the flowmeter 24. However, the range may be changed by either: (1) changing probe 10 to provide a different size outlet orifice such as orifice 18; (2) changing the flowmeter 24; or by (3) changing the first portion 34a of piston 34 to effect a weight change. Any such change or combination thereof is rather quickly and easily made with the embodiment illustrated in FIG. 1. The measuring scale 26 on flowmeter 24 is calibrated in relative permeability values and thus permits ready comparison between various test areas on a mold or core or between different molds or cores.

Figure 2:
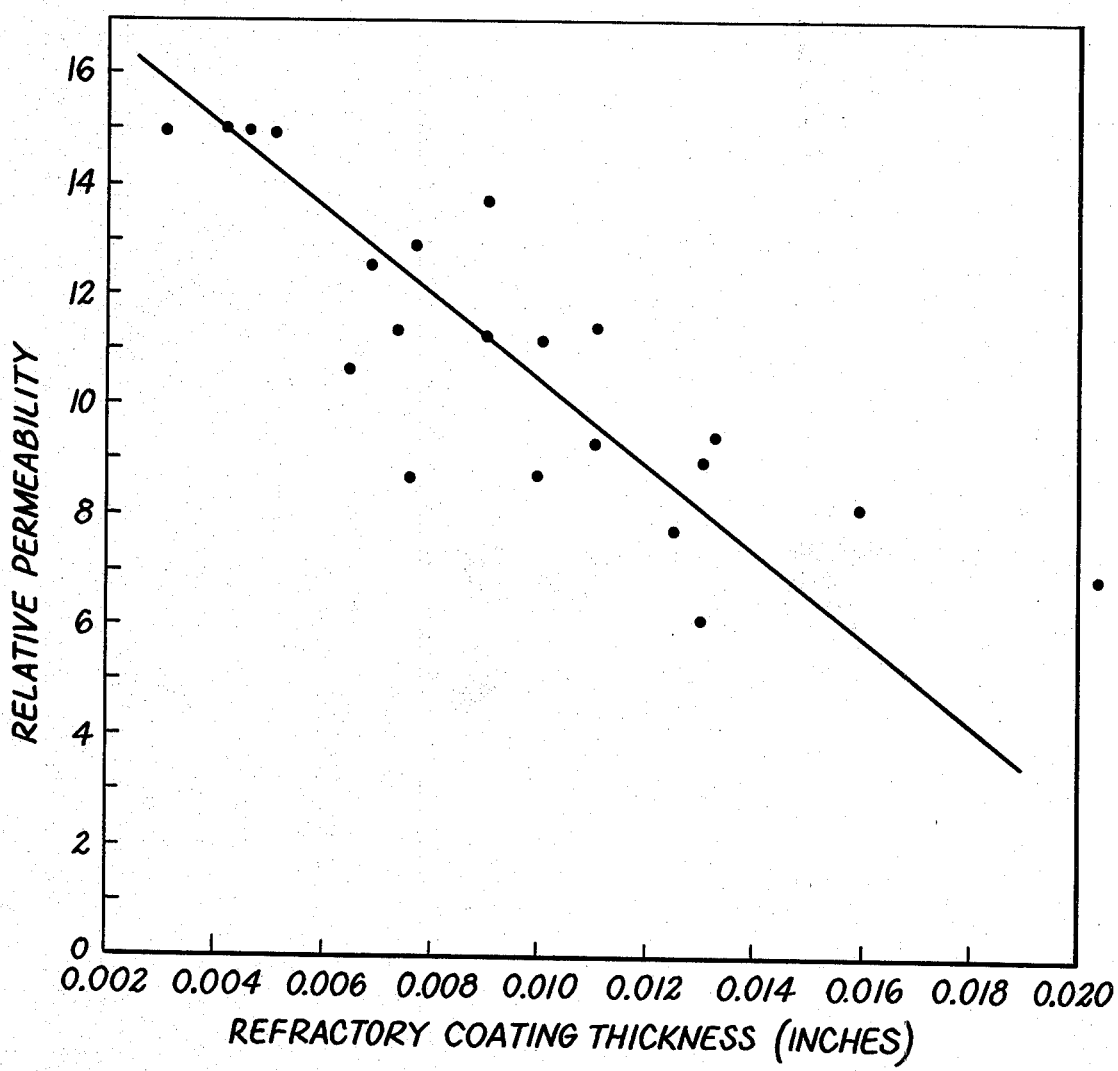
FIG. 2 is an empirically established curve according to the invention, illustrating the relationship between coating thickness on a mold or core (for a particular formulation of a refractory and method of application thereof) and relative permeability as determined by the apparatus of FIG. 1.

To determine the thickness of a refractory coating in place on a mold or core, the apparatus as described above is first used to establish an empirical relationship between coating thickness and relative permeability readings. FIG. 2 illustrates such a relationship in which the ordinant values are relative permeability values taken from flowmeter 24 of FIG. 1. The abscissa values are independently obtained by mechanical gaging techniques. Such mechanical gaging techniques may be destructive of the coating in order to establish the relationship. For example, the coating thickness may be obtained by mechanical micrometer measurements following washing or abrading a portion of the coating away and making corresponding permeability measurements with the apparatus herein described.

Once an empirical relationship such as that of FIG. 2 is established for a particular type of coating, and for its method of application, the relationship may be referred to with permeability measurements made on molds or cores to estimate the thickness of the applied refractory coating. Coating formulations and coating chemical compositions vary, of course, depending on a number of factors so that, preferably, an empirical relationship such as that of FIG. 2 is established for each coating formulation of interest.

The extent of the relationship depends, of course, on the type of coating and the method of application. The present invention thus provides an improved method and apparatus for determining the permeability and thickness of refractory coatings in place on molds and cores. The apparatus has the important advantage of being highly portable, easily operated, and self contained in the exclusion of external connections to sources of air or other utilities.

While the present invention has been disclosed in connection with the preferred embodiment thereof, it should be understood that there may be other embodiments which fall within the spirit and scope of the invention as defined by the following claims.

What is claimed is:

1. Portable apparatus for determining the air permeability of a refractory coating in place upon a foundry mold or core, comprising, a hand-held contact probe having an inlet connection, an outlet orifice of predetermined area adapted for sealing contact with the mold or core, and a passageway fluidly interconnecting said inlet connection and said outlet orifice;

a hand-held measuring unit including a flowmeter having an inlet, an outlet, and a measuring scale calibrated in terms of permeability; a cylinder having a gravity-operated piston sealingly slidable between first and second ends of said cylinder, said first end being fluidly open to the atmosphere and said second end being fluidly connected to the input of said flowmeter; and a gravity-operated check valve connected to admit atmospheric air to said cylinder at said second end; and flexible conduit fluidly interconnecting the outlet of said flowmeter and the inlet of said probe;

whereupon inverting said hand-held measuring unit causes said piston to slide to said first end of said cylinder and said check valve to be opened to admit air to said cylinder so that said piston exerts a constant pressure causing air to flow from said cylinder through said mold at a rate indicative of permeability as determined by said flowmeter when said hand-held unit is repositioned in a non-inverted position and the outlet of said probe is in contact with the mold or core.

2. The apparatus of claim 1 wherein said flowmeter is a variable area flowmeter adapted to be quickly replaced to provide changes in said measuring scale.

3. The apparatus of claim 2 wherein said gravity-operated check valve is a ball check valve.

4. The apparatus of claim 3 wherein said outlet orifice is adapted for sealing contact by affixing a concentric resilient sealing ring around said outlet orifice.

5. The apparatus of claim 4 wherein said flexible conduit is flexible cylindrical tubing.

6. The apparatus of claim 5 wherein said gravity-operated piston comprises first and second portions detachably held together to facilitate changing the weight of said piston by removing and replacing said first portion thereof.

7. A method for estimating, at a test location upon a foundry mold or core, the thickness of refractory coating in place thereupon, comprising the steps of:

(a) establishing an empirical relationship between refractory coating thickness and air permeability of said coating, said permeability being determined by apparatus as defined in claim 1 and said refractory coating thickness being determined by independent means;

(b) determining air permeability at said test location with the apparatus of claim 1; and (c) determining the refractory coating thickness at said test location from the permeability of step (b) and the relationship of step (a).

8. A method of determining the thickness of a refractory coating at a plurality of test locations upon a foundry mold or core, comprising the step of (a) repeating steps (b) and (c) of claim 7 for said plurality of test locations.

* * * * *